(12) United States Patent
Livneh

(10) Patent No.: US 9,737,359 B2
(45) Date of Patent: Aug. 22, 2017

(54) APPARATUS AND METHOD FOR SKIN TIGHTENING AND CORRECTIVE FORMING

(75) Inventor: Steve Livneh, Amherstburg (CA)

(73) Assignee: RF KINETICS INC., Amherstburg, Ontario (CA)

(*) Notice: Subject to any disclaimer, the term of this patent is extended or adjusted under 35 U.S.C. 154(b) by 1319 days.

(21) Appl. No.: 11/773,705

(22) Filed: Jul. 5, 2007

(65) Prior Publication Data

US 2009/0105706 A1 Apr. 23, 2009

Related U.S. Application Data

(60) Provisional application No. 60/818,702, filed on Jul. 5, 2006.

(51) Int. Cl.
*A61B 18/14* (2006.01)
*A61B 18/00* (2006.01)

(52) U.S. Cl.
CPC . *A61B 18/1477* (2013.01); *A61B 2018/00011* (2013.01); *A61B 2018/00291* (2013.01); *A61B 2018/00452* (2013.01); *A61B 2018/143* (2013.01); *A61B 2018/1475* (2013.01)

(58) Field of Classification Search
CPC ........ A61B 18/1477; A61B 2018/1475; A61B 2018/143; A61B 17/07207
USPC .................................. 606/27, 29, 45, 48–50
See application file for complete search history.

(56) References Cited

U.S. PATENT DOCUMENTS

| | | | |
|---|---|---|---|
| 4,920,968 A | 5/1990 | Takase | |
| 5,452,513 A * | 9/1995 | Zinnbauer | A61B 17/0467 30/124 |
| 5,582,611 A * | 12/1996 | Tsuruta | A61B 17/00234 606/142 |
| 5,611,806 A | 3/1997 | Jang | |
| 5,618,295 A | 4/1997 | Min | |
| 5,660,836 A | 8/1997 | Knowlton | |
| 5,755,753 A | 5/1998 | Knowlton | |
| 5,871,524 A | 2/1999 | Knowlton | |
| 5,919,219 A | 7/1999 | Knowlton | |
| 5,948,011 A | 9/1999 | Knowlton | |
| 5,964,729 A | 10/1999 | Choi et al. | |
| 6,241,753 B1 | 6/2001 | Knowlton | |
| 6,277,116 B1 | 8/2001 | Utely et al. | |
| 6,311,090 B1 | 10/2001 | Knowlton | |
| 6,377,854 B1 | 4/2002 | Knowlton | |
| 6,377,855 B1 | 4/2002 | Knowlton | |

(Continued)

OTHER PUBLICATIONS

International Search Report and Written Opinion for PCT Application No. PCT/US2007/015441 mailed on Jan. 31, 2008; 9 pages.

*Primary Examiner* — Jaymi Della
(74) *Attorney, Agent, or Firm* — Howard & Howard Attorneys PLLC

(57) ABSTRACT

An electrosurgical apparatus applies electrical current to skin, preferably for skin tightening procedures. A housing includes a substantially flat edge, disposable on the skin. The housing stores a plurality of electrodes which are movable through an opening defined by the edge. A vacuum is applied in the housing such that the edge seals with the skin. The electrodes pierce the skin perpendicularly and apply an RF electric current to heat primarily the subcutaneous layer. A coolant is applied to cool the outer layer of the skin.

25 Claims, 13 Drawing Sheets

(56) References Cited

U.S. PATENT DOCUMENTS

| | | |
|---|---|---|
| 6,381,497 B1 | 4/2002 | Knowlton |
| 6,381,498 B1 | 4/2002 | Knowlton |
| 6,387,380 B1 | 5/2002 | Knowlton |
| 6,391,038 B2* | 5/2002 | Vargas ............... A61B 17/064 227/175.1 |
| 6,405,090 B1 | 6/2002 | Knowlton |
| 6,428,538 B1* | 8/2002 | Blewett ............. A61B 18/1485 606/41 |
| 6,453,202 B1 | 9/2002 | Knowlton |
| 6,556,869 B1 | 4/2003 | Leonard et al. |
| 6,697,670 B2 | 2/2004 | Chomenky |
| 6,743,211 B1 | 6/2004 | Prausnitz |
| 6,795,728 B2 | 9/2004 | Chomenky |
| 6,892,099 B2 | 5/2005 | Jaafar |
| 7,013,179 B2 | 3/2006 | Carter et al. |
| 7,130,696 B2 | 10/2006 | Carter et al. |
| 7,585,297 B2 | 9/2009 | Baker |
| 7,824,394 B2 | 11/2010 | Manstein |
| 8,007,493 B2 | 8/2011 | McGill et al. |
| 8,133,216 B2 | 3/2012 | Knopp et al. |
| 8,135,475 B2 | 3/2012 | Kreindel et al. |
| 2002/0120260 A1* | 8/2002 | Morris et al. ................. 606/41 |
| 2003/0153905 A1* | 8/2003 | Edwards et al. .............. 606/41 |
| 2003/0216727 A1* | 11/2003 | Long ................... A61B 18/1492 606/41 |
| 2005/0145671 A1* | 7/2005 | Viola ............... A61B 17/00491 227/175.1 |
| 2005/0159778 A1* | 7/2005 | Heinrich ............. A61B 17/072 606/216 |
| 2006/0085056 A1 | 4/2006 | Schouenborg |
| 2006/0089688 A1 | 4/2006 | Panescu |
| 2007/0142885 A1 | 6/2007 | Hantash et al. |
| 2008/0082090 A1 | 4/2008 | Manstein |
| 2009/0093864 A1 | 4/2009 | Anderson |
| 2009/0112205 A1* | 4/2009 | McGill ................. A61B 18/14 606/41 |
| 2010/0023003 A1 | 1/2010 | Mulholland |
| 2010/0116867 A1* | 5/2010 | Balbierz ............. A61B 17/068 227/175.1 |
| 2011/0009737 A1 | 1/2011 | Manstein |
| 2011/0046615 A1 | 2/2011 | Manstein |
| 2011/0092884 A1 | 4/2011 | Kang |
| 2011/0130618 A1 | 6/2011 | Ron Edoute et al. |
| 2011/0190726 A1 | 8/2011 | Hantash |
| 2011/0270364 A1 | 11/2011 | Kreindel et al. |
| 2012/0150266 A1 | 6/2012 | Shalev et al. |
| 2012/0158100 A1 | 6/2012 | Schomacker |

* cited by examiner

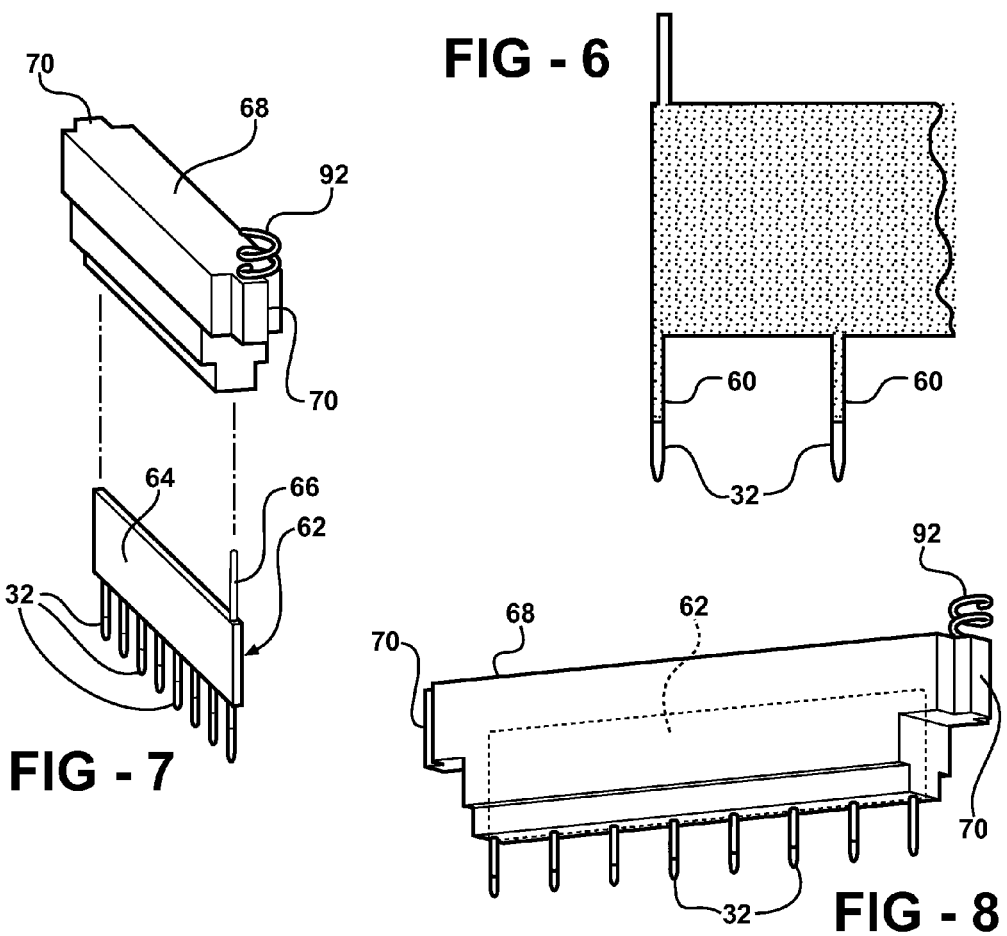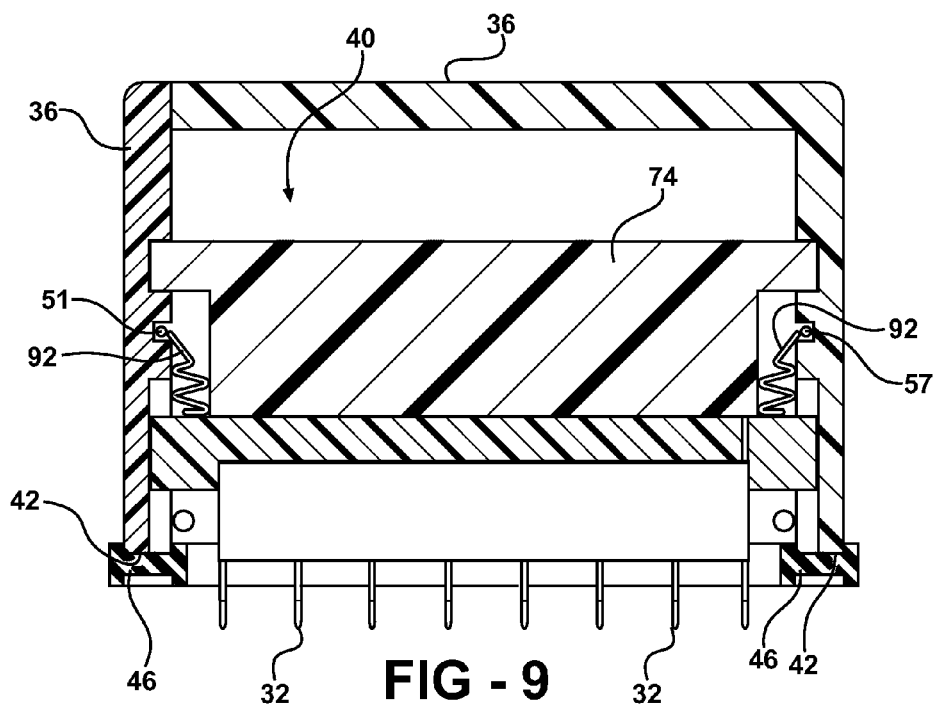

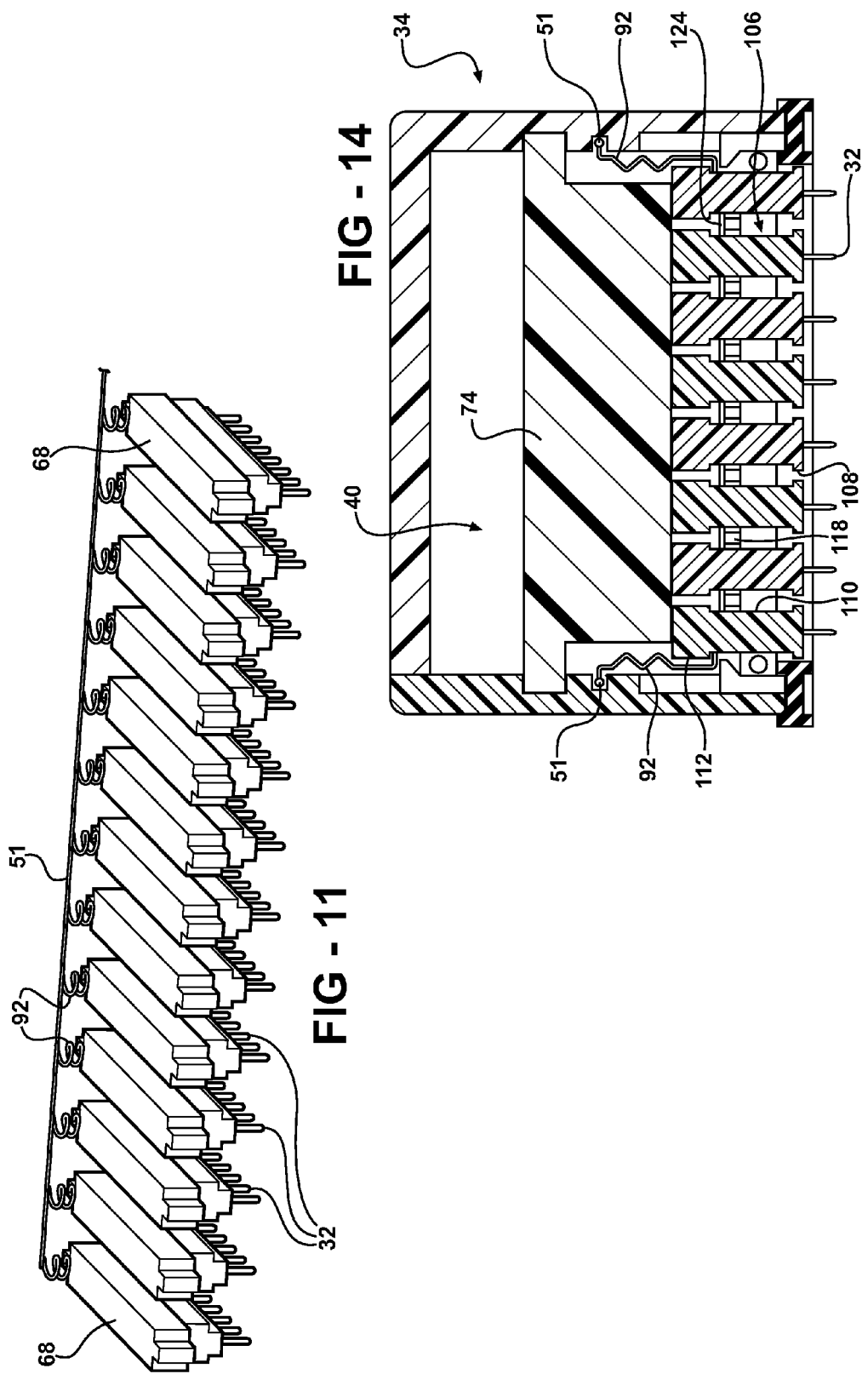

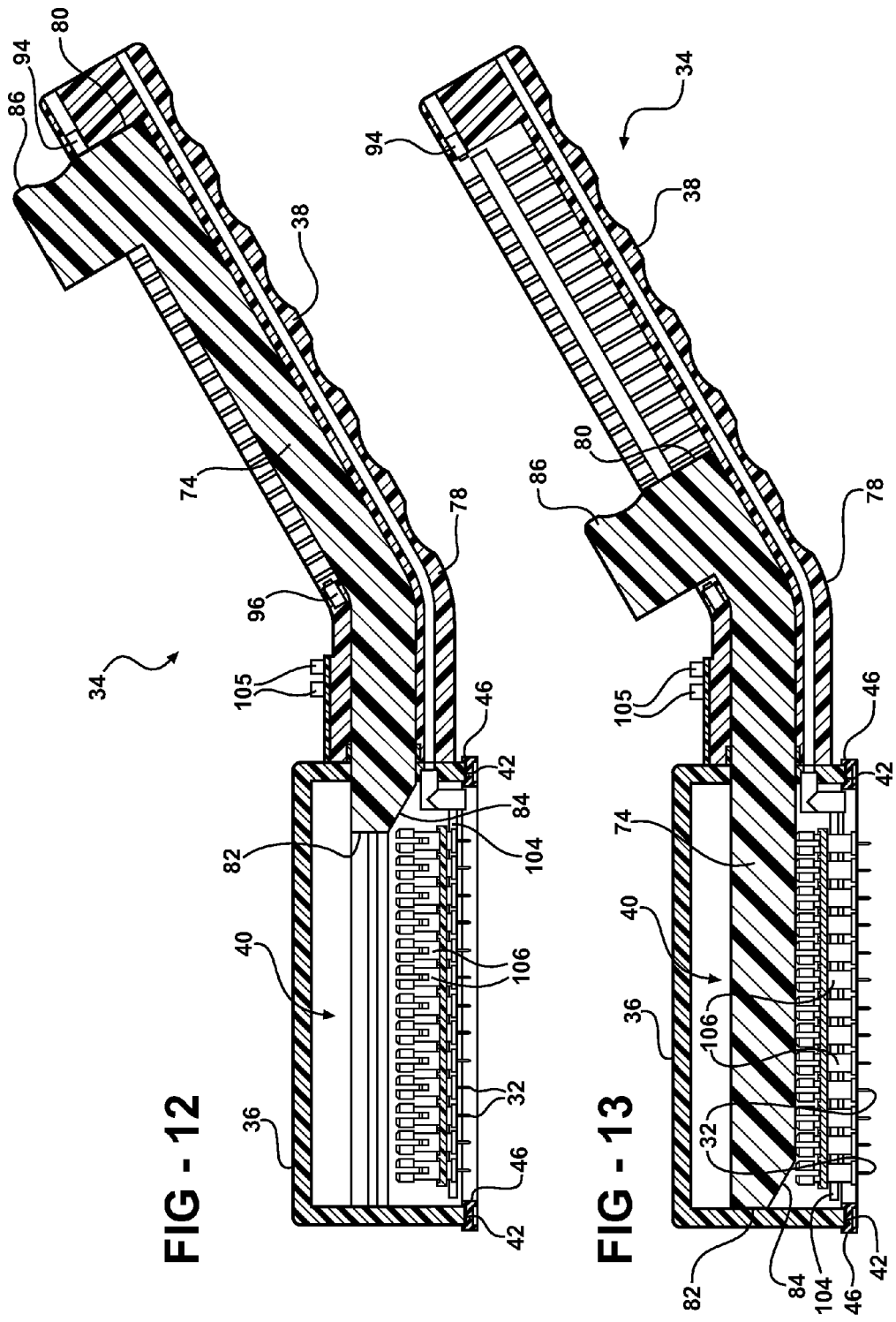

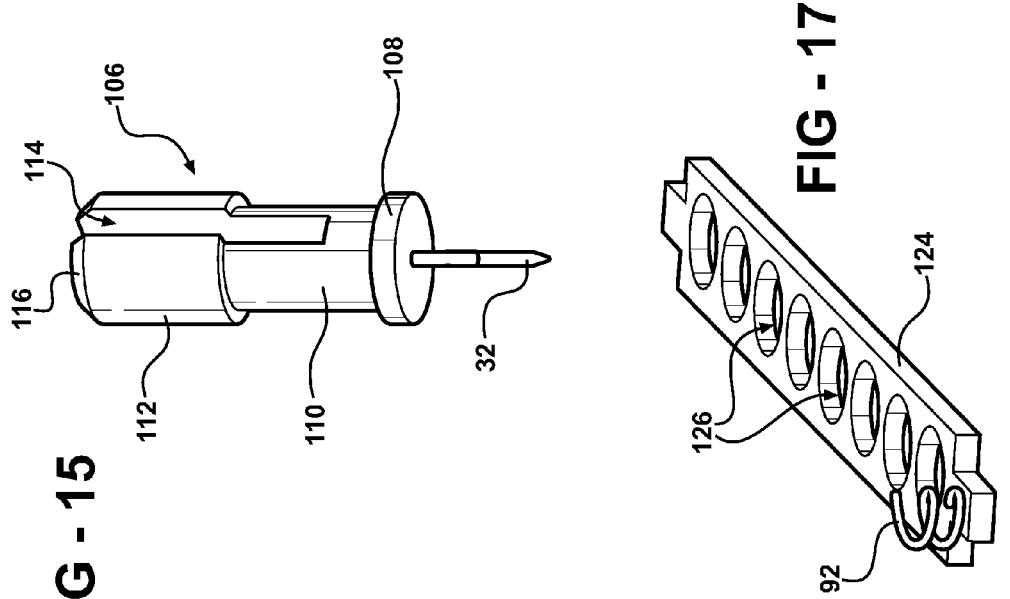
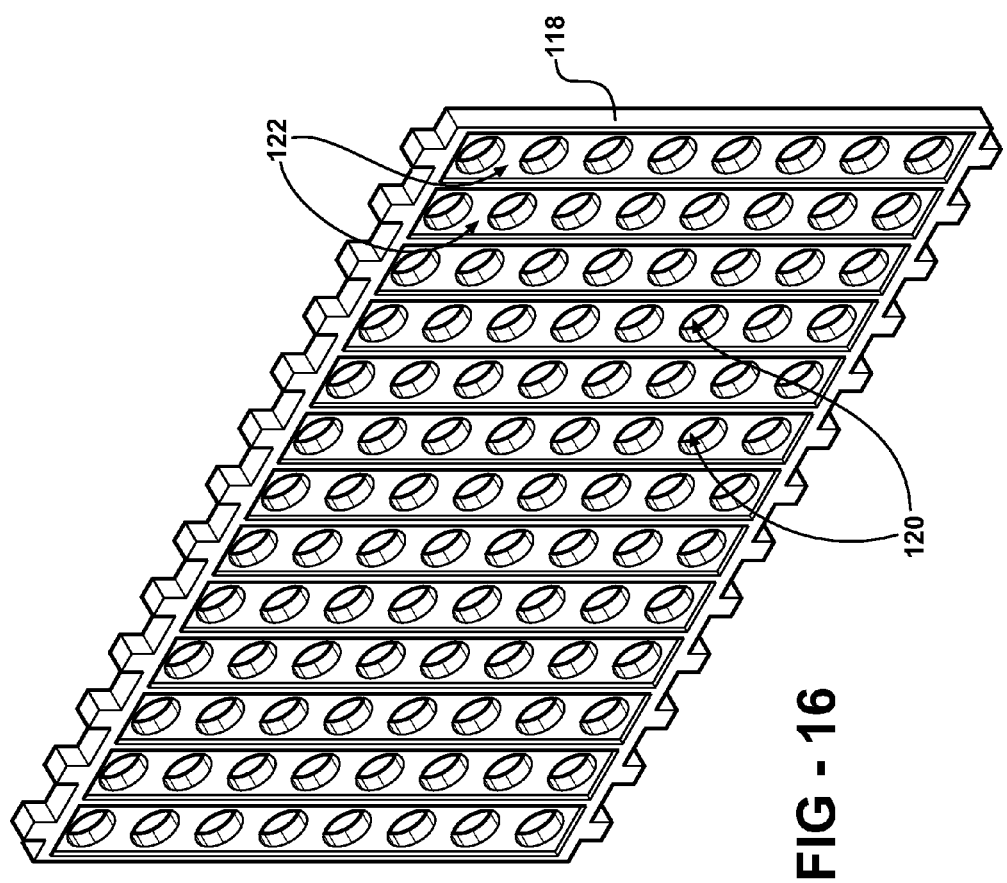

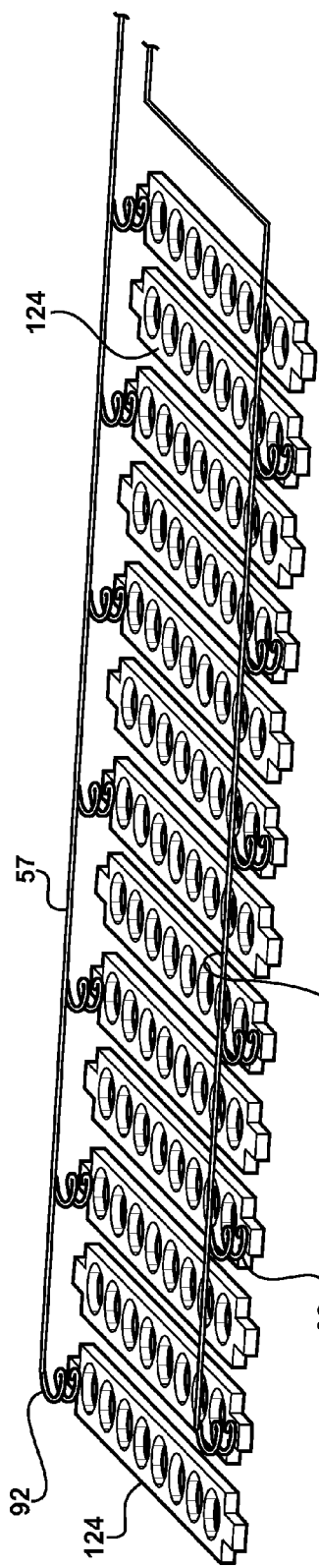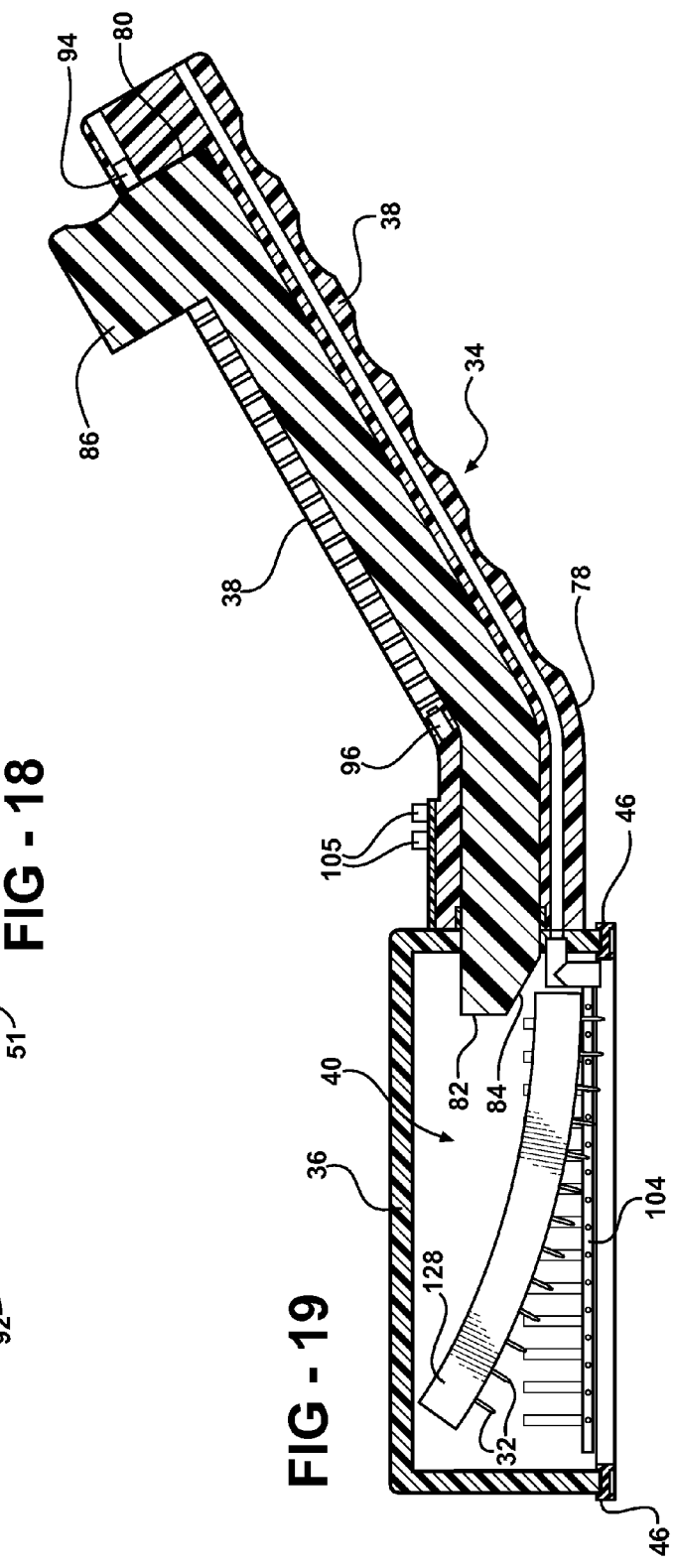

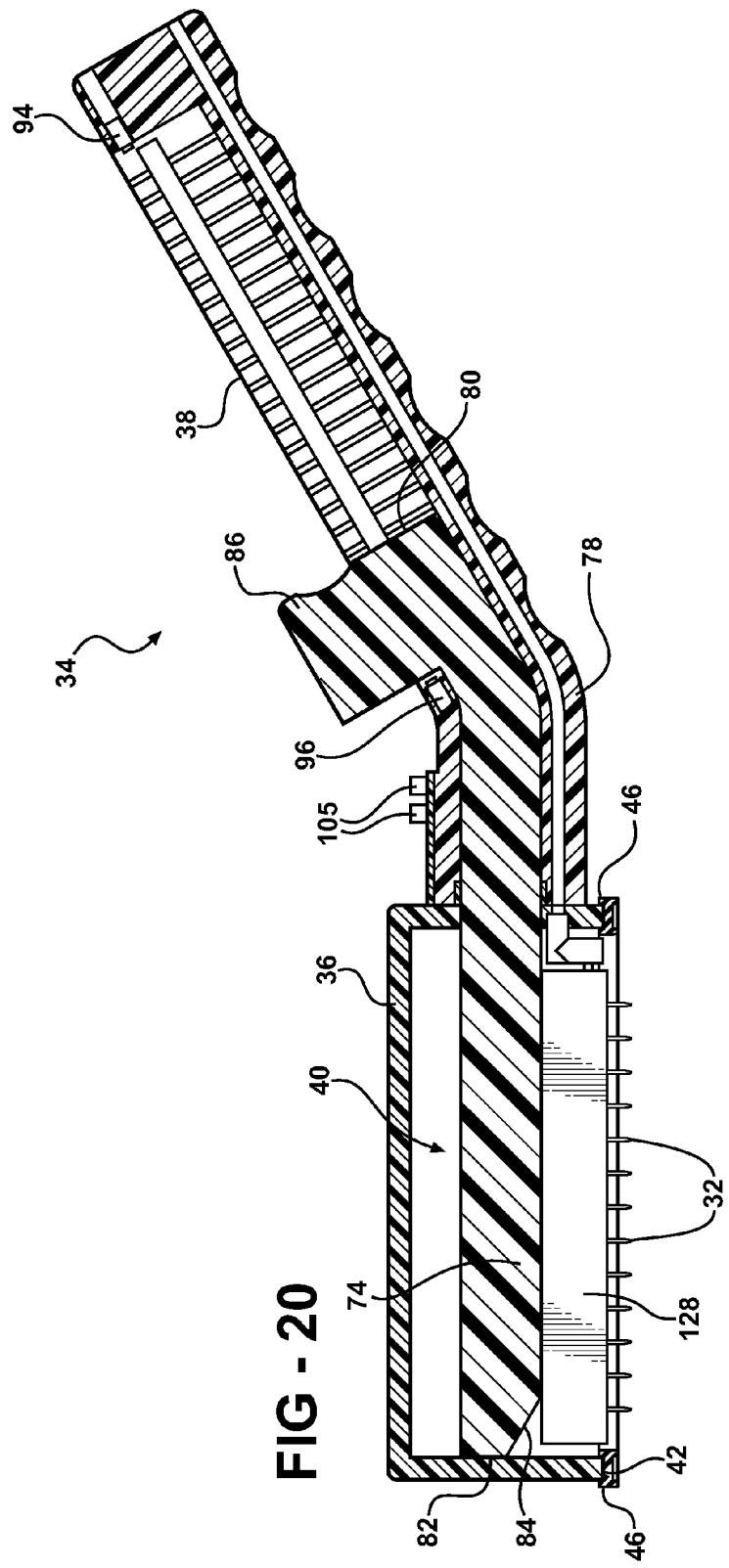

APPARATUS AND METHOD FOR SKIN TIGHTENING AND CORRECTIVE FORMING

CROSS REFERENCE TO RELATED APPLICATION

The subject patent application claims priority to and all the benefits of U.S. Provisional Patent Application Ser. No. 60/818,702 which was filed on Jul. 5, 2006, the entire specification of which is expressly incorporated herein by reference.

BACKGROUND OF THE INVENTION

1. Field of the Invention

This invention relates to an apparatus and method for skin tightening. More specifically, the present invention provides an apparatus and method for introducing thermal and mechanical injury to skin via electrodes carrying an electric current.

2. Description of the Prior Art

Achieving a younger looking skin having tight and well defined contours is commonly desired. Traditional devices tighten the skin by applying radio frequency (RF) energy to the surfaced of the skin. An example of a device used to tighten the skin by applying RF energy to the surface of the skin is disclosed in U.S. Pat. No. 5,755,753 to Knowlton (the '753 patent). The '753 patent discloses a device connected to an RF generator. The device includes a porous membrane which is inflated with an electrolytic solution. Once inflated, the membrane conforms to the surface of the skin. The membrane imparts a cooling effect to the skin. A plurality of electrodes are positioned at various locations in the membrane. The generator is coupled to the electrodes and a source for the electrolytic solution is coupled to the membrane. The electrodes impart radiant energy to the layers of the skin. This energy heats the skin and the underlying collagen tissue. As a result of the application of the energy to the surface of the skin, the collagen transforms its structure and contracts.

However, there exists a need for a skin tightening device which combines the benefits of applying thermal and mechanical injury.

SUMMARY OF THE INVENTION AND ADVANTAGES

The subject invention provides an electrosurgical apparatus for applying electrical current to skin. The apparatus includes a housing having an edge defining an opening. The edge is disposable on the skin. A plurality of electrodes conveys the electrical current to the skin. Each of the electrodes is movable between a first position and a second position. An electrode positioning mechanism is operatively engagable with the plurality of electrodes for moving each of the electrodes between the first position and the second position. The edge includes a plurality of edge segments that are coplanar with one another.

The apparatus of the subject invention may also include a vacuum pump in fluid communication with the cavity. The edge of the housing sealingly engages with the skin when a vacuum is applied.

The apparatus of the subject invention may also include a coolant supply in fluid communication with the cavity. The coolant is direct applied to the skin.

The electrosurgical apparatus provides numerous advantageous over the prior art. By providing a substantially flat edge, a defined area of skin may be treated with the electrodes. The vacuum and the edge seal the defined area of skin from outside elements to enclose the treated area of skin. While the skin is being heated with the electrodes, the coolant acts to cool the skin to avoid damage to the outer layers of the skin. Since the apparatus of the subject invention applies the coolant directly to the skin, the cooling is done in the most efficient manner.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 6 is a partial front view of a comb of electrodes of the first embodiment;

FIG. 7 is an exploded perspective view of the comb of electrodes and a holder;

FIG. 8 is a perspective view of the holder holding the comb of electrodes;

FIG. 9 is a cross-sectional front view of the first embodiment of the handheld unit showing the electrode positioning mechanism engaging the holder;

FIG. 11 is an exploded perspective view of a plurality of holders connected by a wire in the monopolar operation;

FIG. 12 is a cross-sectional side view of a second embodiment of the handheld unit showing the electrode positioning mechanism in the first position;

FIG. 13 is a cross-sectional side view of a second embodiment of the handheld unit showing the electrode positioning mechanism in the second position;

FIG. 14 is a cross-sectional front view of the second embodiment of the handheld unit showing the electrode positioning mechanism engaging capsules supporting the electrodes;

FIG. 15 is a perspective view of one of the capsules of the second embodiment supporting one of the electrodes;

FIG. 16 is a perspective view of a plate of the second embodiment for supporting a plurality of capsules;

FIG. 17 is a perspective view of a conductive strip of the second embodiment for conducting electrical current to a plurality of capsules;

FIG. 18 is an exploded perspective view of a plurality of plates connected by wires in the bipolar operation;

FIG. 19 is cross-sectional side view of a third embodiment of the handheld unit showing the electrode positioning mechanism in the first position;

FIG. 20 is cross-sectional side view of the third embodiment of the handheld unit showing the electrode positioning mechanism in the second position;

DETAILED DESCRIPTION OF THE INVENTION

Figure 1:
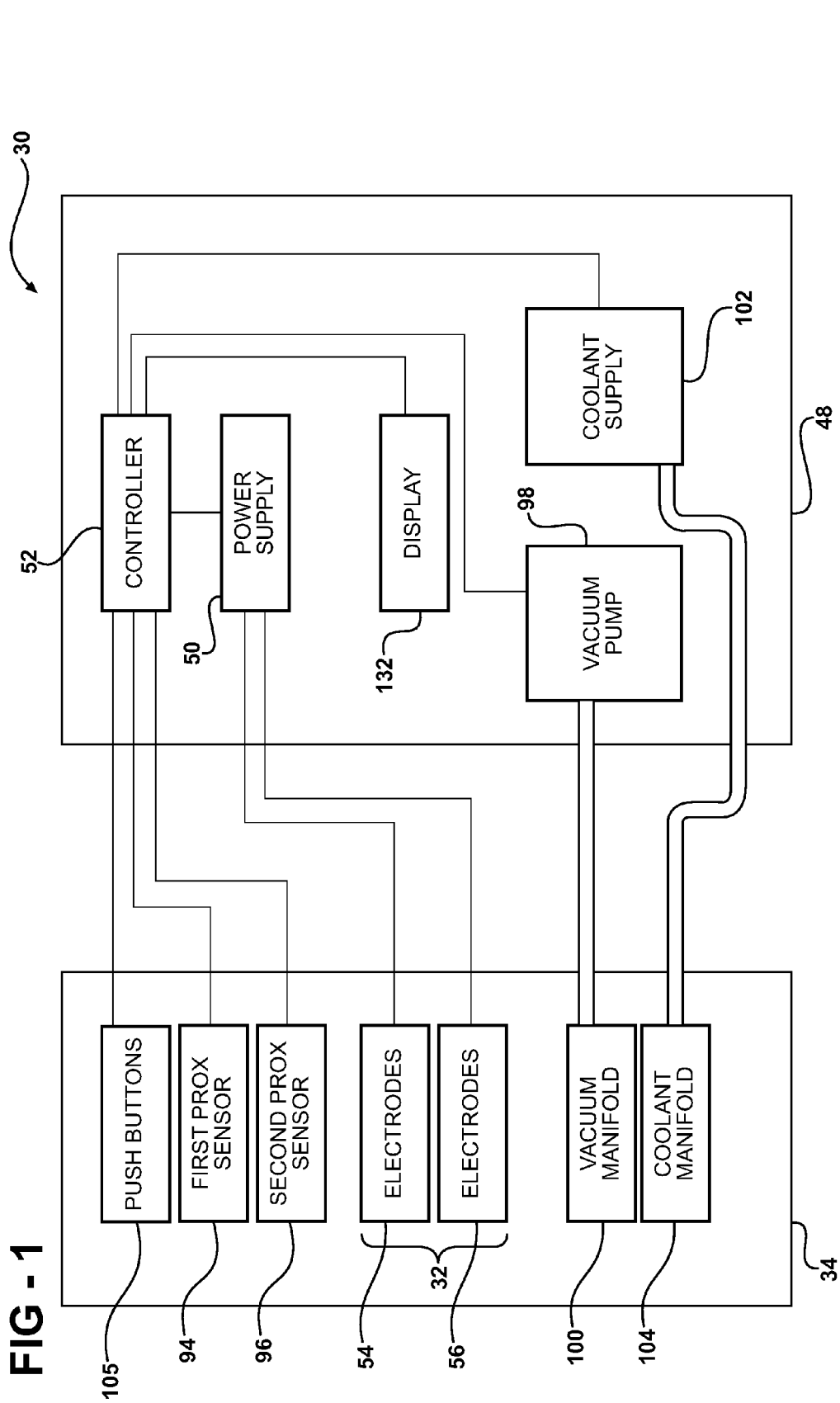
FIG. 1 is a block diagram of an electrosurgical apparatus showing interconnections between a handheld unit and a control unit in a bipolar operation.

Referring to the Figures, wherein like numerals indicate corresponding parts throughout the several views, an electrosurgical apparatus 30 is shown in FIG. 1. The apparatus 30 is capable of delivering electrical current to skin using a plurality of electrodes 32 which enter the skin. Preferably, the apparatus 30 is utilized in skin tightening procedures. However, other uses of the apparatus 30 will be evident to those skilled in the art.

Figure 2:
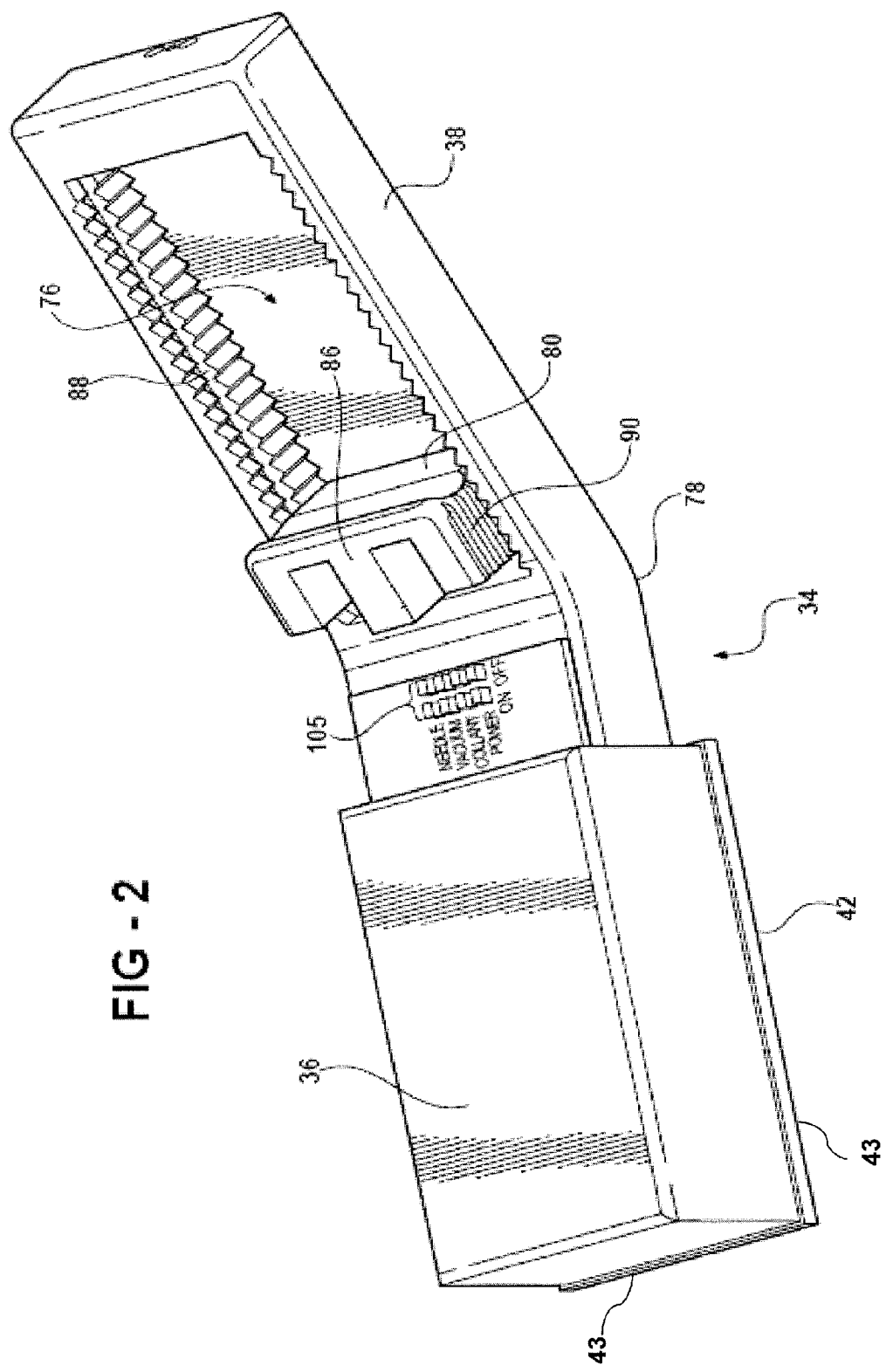
FIG. 2 is a perspective view of the handheld unit showing an electrode positioning mechanism in a second position.
Figure 3:
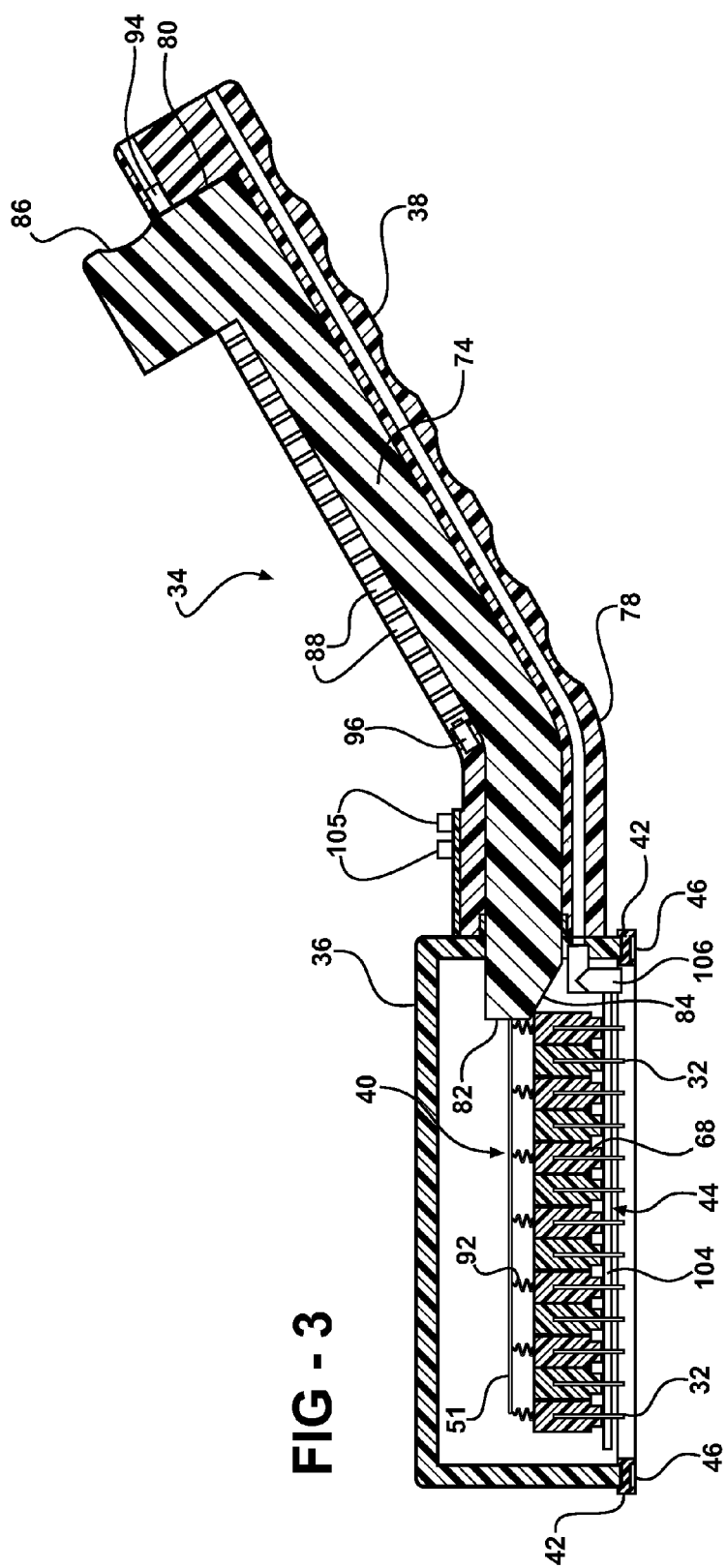
FIG. 3 is a cross-sectional side view of a first embodiment of the handheld unit showing the electrode positioning mechanism in a first position.
Figure 4:
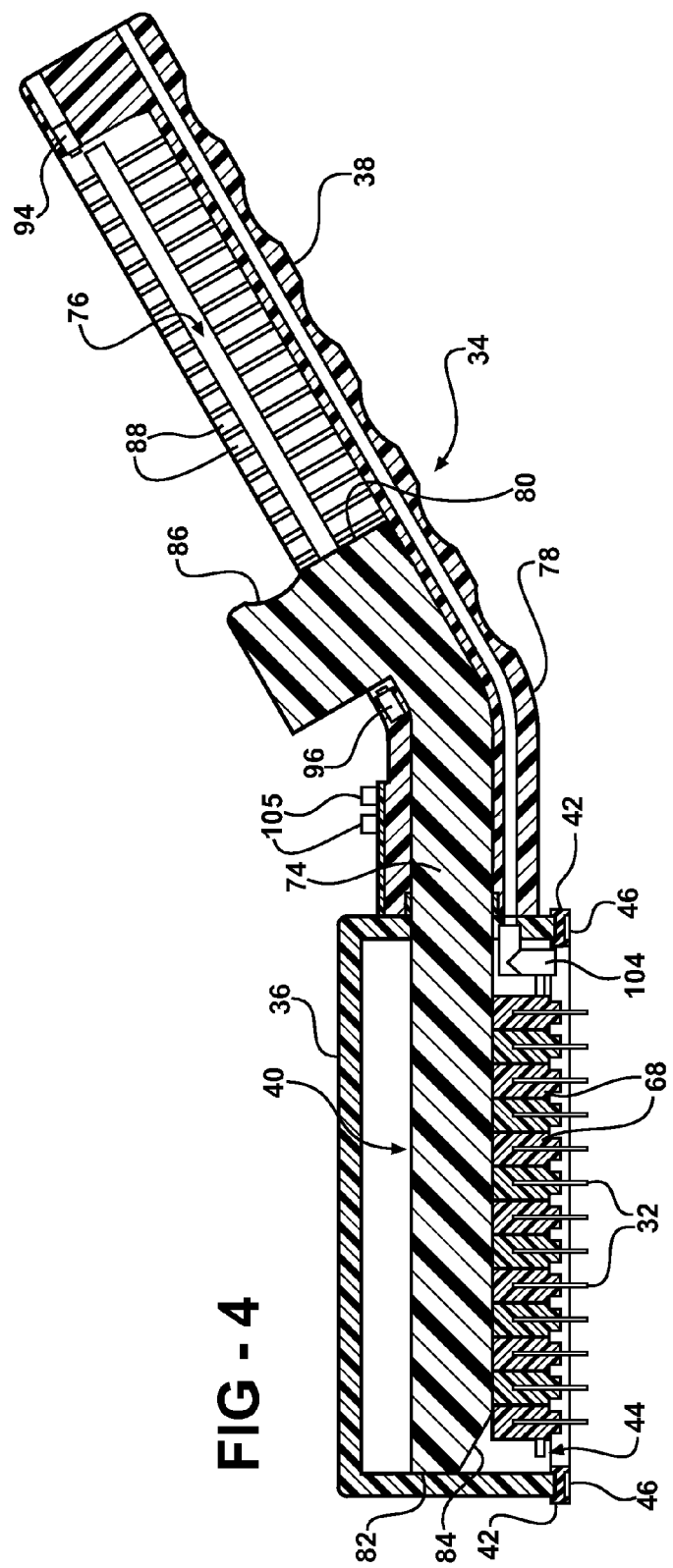
FIG. 4 is a cross-sectional side view of a first embodiment of the handheld unit showing the electrode positioning mechanism in the second position.

The apparatus 30 includes a handheld unit 34, as shown in FIG. 2. Referring to FIGS. 3 and 4, the handheld unit 34 includes a housing 36 for supporting and concealing the plurality of electrodes 32 as well as other components described in greater detail below. The housing 36 is preferably formed of plastic; however, other materials may also be suitable, including, but not limited to, fiberglass or metal. The housing 36 is connected to a handle portion 38. The handle portion 38 designed to be held by an operator of the apparatus 30, such as a physician, nurse, or technician.

The housing 36 defines a cavity 40 in which the electrodes 32 are concealed when not in operation. The housing 36 includes an edge 42 defining an opening 44 providing access to the cavity 40. The edge 42 includes a plurality of edge segments 43. The edge segments 43 are coplanar with one another. Thus, the edge 42 forms a substantially flat surface. The edge 42 preferably also includes a seal 46 formed of an elastomeric material, such as rubber. However, other materials may be utilized to form the seal 46. The edge 42 and/or the seal 46 are disposable on the skin as is described in greater detail below.

Preferably, each of the electrodes 32 is generally perpendicular with the edge when the electrode 32 is in the second position. Said another way, the electrode 32 extends "straight into" the skin at about a 90 degree angle. This direction of entry causes the least damage to the skin to quicken surgical recovery time.

Referring again to FIG. 1, the apparatus 30 also includes a control unit 48. The control unit 48 is preferably separate from the handheld unit 34 to manage the overall weight of the handheld unit 34. However, those skilled in the art realize that some or all of the features of the control unit 48 may be incorporated within the handheld unit 34 if desired.

The control unit 48 includes a power supply 50 for supplying the electrical current to the electrodes 32. The power supply 50 preferably converts commercial AC electrical power, e.g., a 120 volt, 60 hertz signal, to a radio frequency (RF) signal, i.e., an AC signal operating at a radio frequency. Preferably, a cable (not shown) or other electrical connection allows transmission of the RF signal from the power supply 50 in the control unit 48 to the electrodes 32 in the handheld unit 34. One or more wires 51 are preferably disposed within the housing 36 of the handheld unit 34 to conduct the RF signal within the handheld unit 34.

The control unit 48 also preferably includes a controller 52 for controlling operation of the apparatus 30. The controller 52 is preferably implemented as a microprocessor-based device. However, the controller 52 may be implemented as a logic circuit or other implementation as well known to those skilled in the art.

Figure 5:
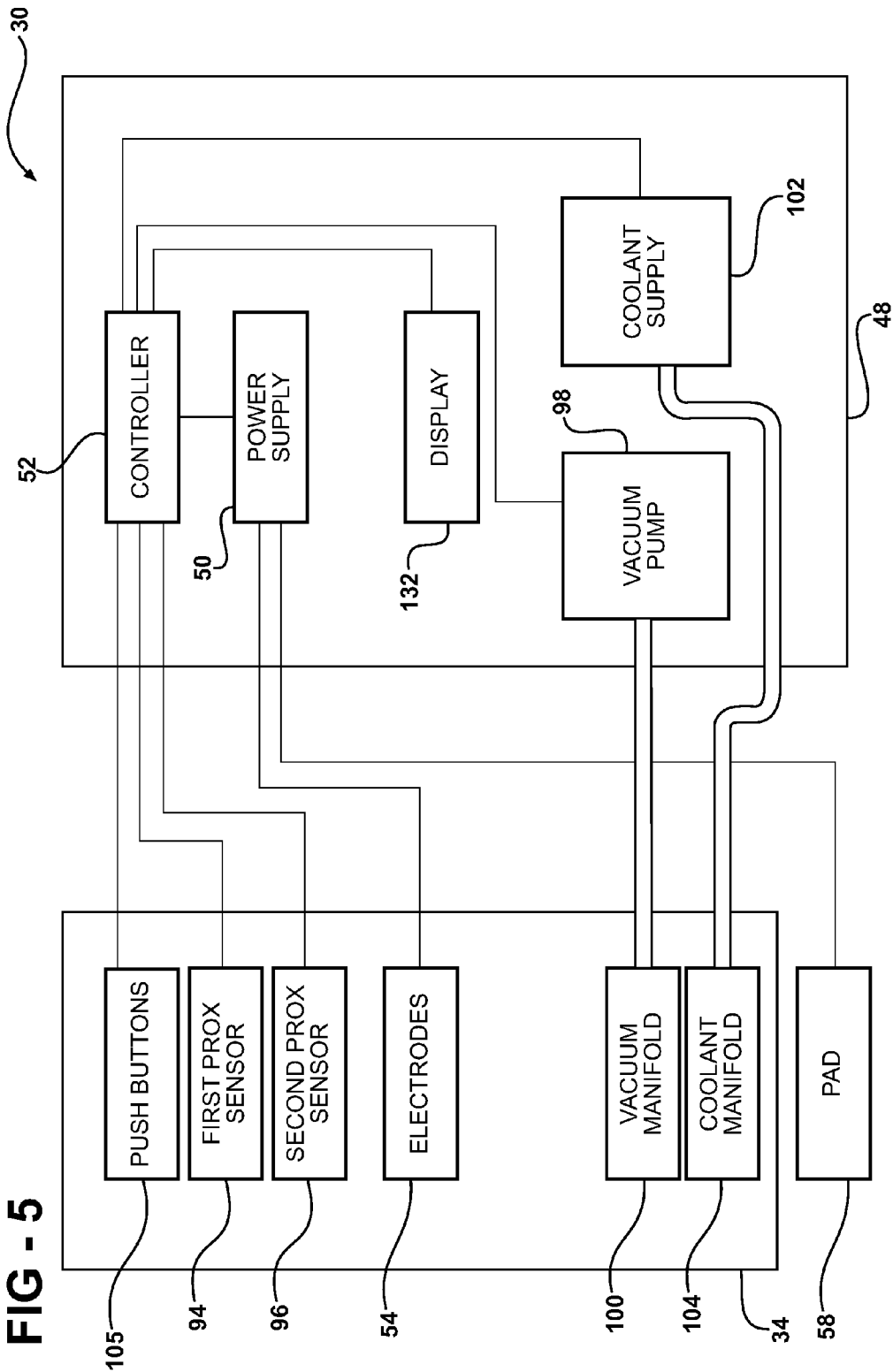
FIG. 5 is a block diagram of the electrosurgical apparatus showing interconnections between the handheld unit and the control unit in a monopolar operation.

The apparatus 30 may be configured for either bipolar or monopolar operation. Specifically, in bipolar operation, as shown in FIG. 1, the RF signal is applied through a first set 54 of the electrodes 32 and utilizes a second set 56 of electrodes 32 as a return path to the power supply 50. In monopolar operation, as shown in FIG. 5, the RF signal is applied through all of the electrodes 32 and a pad 58, connectable to the skin of the patient, provides the return path to the power supply 50.

Referring now to FIG. 6, the electrodes 32 are preferably formed of a metal such that they are electrically conductive. Most preferably, the electrodes 32 are formed of stainless steel, but other suitable materials are known to those skilled in the art. Each electrode 32 is preferably shaped like a needle. That is, an end of each electrode forms a sharp, angled point allowing the electrode 32 to puncture the skin.

As mentioned above, the electrodes 32 convey electrical current to the skin. Preferably, each electrode 32 is partially coated with a dielectric, i.e., nonconductive, coating 60. The dielectric coating 60 acts as an insulator to prevent the conduction of the electric current out of the electrode 32 at areas of the electrode 32 covered by the coating. More preferably, about 0.5 mm of each electrode, at a tip end of the electrode, is uncoated with the dielectric coating. Thus, the electric current flows from the electrode at the tip end.

Each of the electrodes 32 is movable between a first position and a second position. In the first position, as shown in FIG. 3, the electrode 32 is completely concealed within the cavity 40 formed by the housing 36, i.e., the electrode 32 does not protrude through the opening 44. The first position may be referred to as the retracted position. In the second position, as shown in FIG. 4, the electrode 32 protrudes through the opening 44. This second position may be referred to as an extended position. When the edge 42 and/or seal 46 is disposed on the skin of the patient, the electrode 32 will pierce the skin in the second position.

The apparatus includes an electrode positioning mechanism 74 operatively engageable with the electrodes 32 for moving the electrodes 32 between the first and second positions. The mechanism 74 operatively engages at least one electrode 32 as it moves. Preferably, however, the mechanism 74 operatively engages at least two of the plurality of electrodes 32 simultaneously such that the at least two electrodes 32 move between the positions in unison. The handle portion 38 defines at least one channel 76 that accommodates the mechanism 74. The mechanism 74 slidably engages the handle portion 38 while sliding through the channel 76.

The handle portion 38 includes at least one bend 78 such that part of the handle portion 38 is non-parallel to the edge 42 of the housing 36, as shown in FIGS. 3 and 4. The mechanism 74 must be flexible to accommodate the change in direction provided by the bend 78 and other contours formed by the housing 36. Preferably, the mechanism 74 is preferably formed of an elastomeric material. Alternatively, the mechanism 74 may be formed of any other flexible material. Furthermore, it is preferred that the mechanism 74 is non-conductive or coated with a non-conductive material.

The mechanism 74 includes a proximal end 80 and a distal end 82. The distal end 82 is tapered to provide an angled surface 84 for operatively engaging the electrodes 32 as the mechanism 74 is moved from the first position to the second position. Referring primarily to FIG. 2, the proximal end 80 of the mechanism includes an engagement tab 86. The engagement tab 86 allows manual operation of the mechanism 74 by the user. The engagement tab 86 and handle portion 38 mechanically engage one another to prevent unintended movement of the mechanism 74 towards the first position. Specifically, the housing 34 defines saw-tooth stubs 88 projecting into the channel 76 and the engagement tab 86 includes ribs 90 for engaging the stubs 88. To release the engagement tab 86, the user squeezes walls (not numbered) of the tab 86 together to release the ribs 80 from the stubs 88 and allow the mechanism 74 to slide freely. Of course, other manual techniques for preventing movement of the mechanism 74 are known to those skilled in the art. Furthermore, automatically powered techniques, e.g., a motor, may be implemented to move the mechanism 74 between the first and second positions.

Referring to FIGS. 3 and 4, the handheld unit 34 preferably includes at least one sensor 94, 96 for sensing the position of the mechanism. Preferably, the at least one sensor 94, 96 is implemented as a first proximity sensor 94 disposed adjacent one longitudinal end of the channel 76 and a second proximity sensor 96 disposed adjacent the other longitudinal end of the channel 76. The proximity sensors 94, 96 sense the presence of the engagement tab 86 of the electrode positioning mechanism 74. The first proximity sensor 94 senses when the mechanism 74 is fully retracted, i.e., when the mechanism 74 is not engaging any of the electrodes 32, such that all electrodes 32 are in the first position. The second proximity sensor 96 senses when the mechanism 74 is fully extended, i.e., when the mechanism 74 is engaging all of the electrodes 32, such that all electrodes 32 are in the second position. The proximity sensors 94, 96 are in communication with the controller 52 to communicate the position of the mechanism 74 to the controller 52. Preferably, a communications cable (not shown) electrically connects the proximity sensors 94, 96 to the controller.

FIGS. 3, 4, and 6-10 illustrate a first embodiment of the invention. In the first embodiment, the electrodes 32 are arranged into a plurality of combs 62. Referring now to FIG. 7, each comb 62 is preferably formed of a single piece of metal which defines several electrodes 32. Preferably, a flat section 64 electrically connects the electrodes 32 of each comb 62 together. A pin 66 extends from the flat section 64 opposite the electrodes 32 to allow electrical connection to the comb 62. Preferably, the flat section 64 of each comb is insulated with a dielectric coating. It is also preferred that a portion of each electrode 32 is insulated with the dielectric coating, as described above, to leave about 0.5 mm of each electrode 32 exposed to conduct the electrical current.

Figure 10:
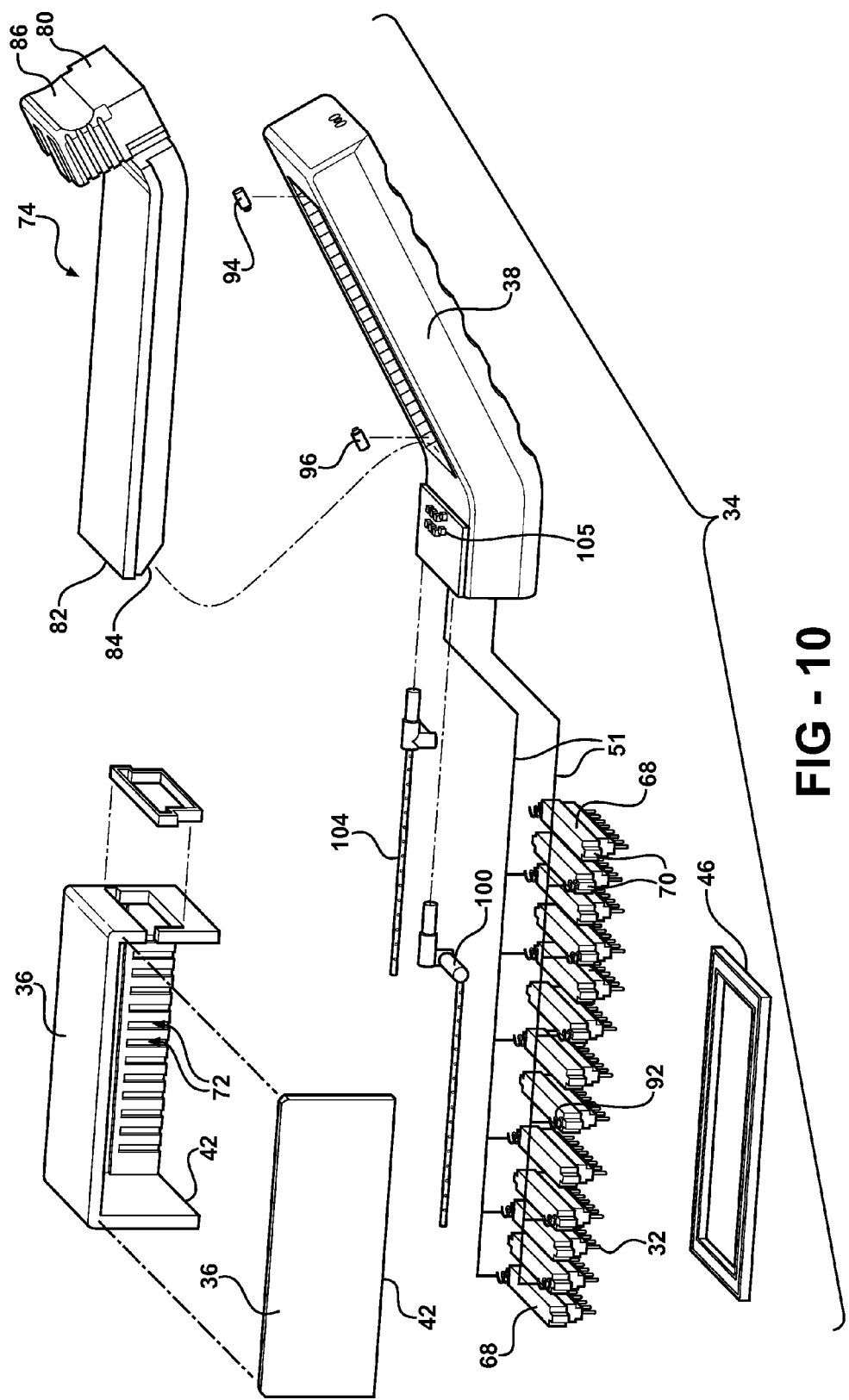
FIG. 10 is an exploded perspective view of the first embodiment of the handheld unit.
Figure 21:
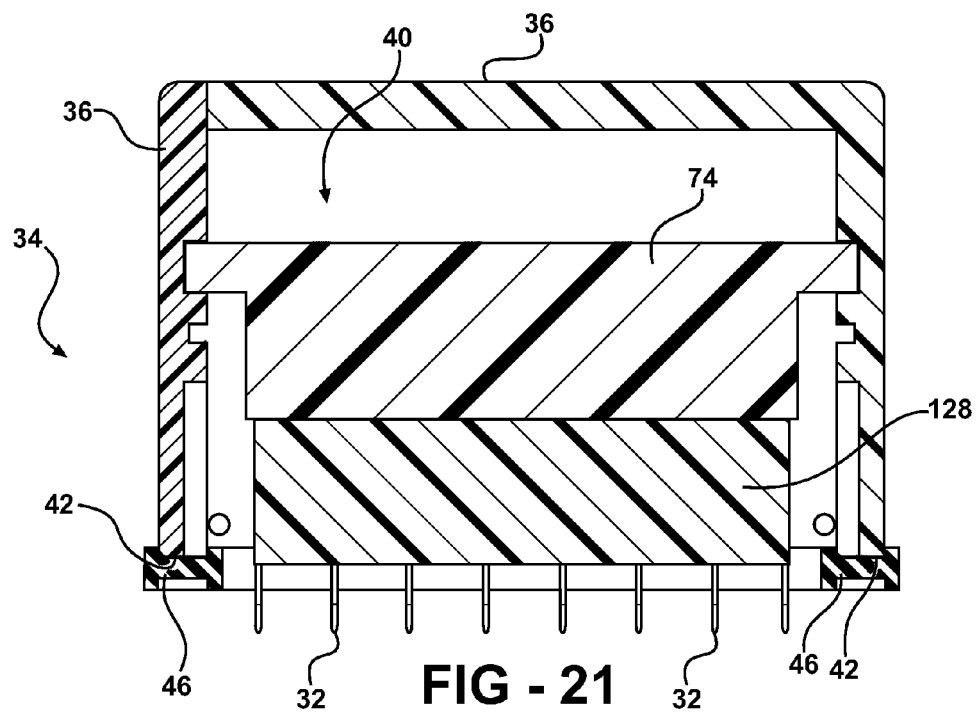
FIG. 21 is a cross-sectional front view of the third embodiment of the handheld unit showing the electrode positioning mechanism engaging a block supporting the electrodes.
Figure 22:
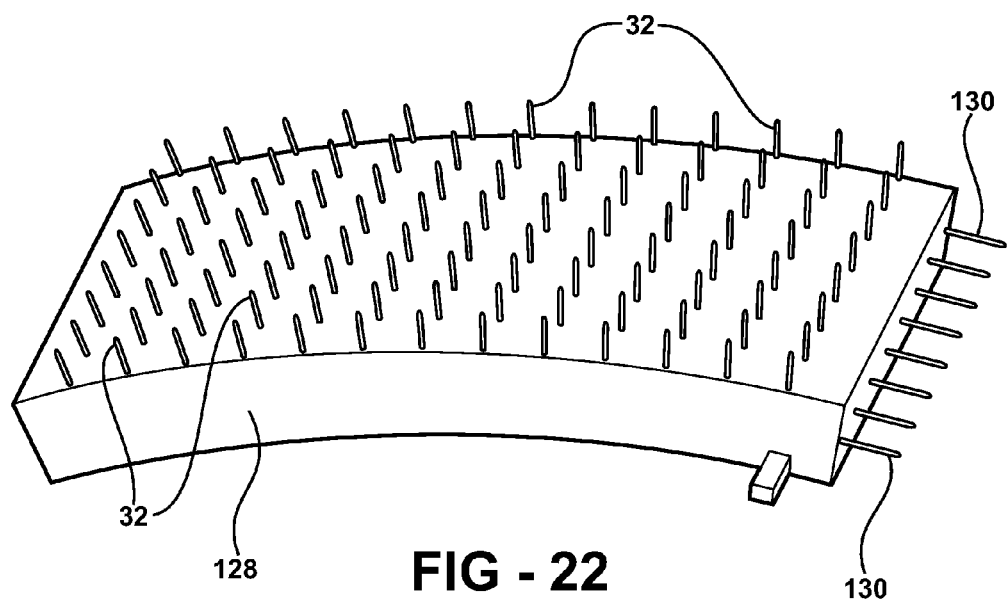
FIG. 22 is a perspective view of the block of the third embodiment.

The electrodes 32 are preferably carried by an electrode carrier (not numbered). In the first embodiment, each comb 62 is supported by a holder 68, as shown in FIGS. 7 and 8. The holder 68 is preferably formed of a non-conductive, i.e., insulating material, such as plastic. Each holder 68 includes a pair of tabs 70 to slidably engage in grooves 72 defined in the housing 36 of the handheld unit 34. The grooves 72 are best observed with reference to FIG. 10. Thus, the holder 68 may slide to move the electrodes 32 from the first to the second position when engaged by the electrode positioning mechanism 74. As can be seen in FIGS. 3, 9, and 10, the combs 62 and holders 68 are arranged in successive rows.

At least one coil 92 extends from a top of each holder 68 to return the holder 68 and the electrodes 32 to the first position after retreat of the mechanism 74. Preferably, the coil 92 electrically connects the comb 92 to one of the wires 51. In the bipolar configuration, as shown in FIG. 10, the coil 92 of each holder 68 in successive rows alternates between the two wires 51, where one wire 51 provides a supply path from the power supply 50 and the other wire 51 provides a return path. In the monopolar configuration, as shown in FIG. 11, only one wire 51 is utilized as a supply path.

The apparatus 30 includes a vacuum pump 98, preferably disposed within the control unit 48, as shown in FIG. 1. The vacuum pump 98 is operatively connected to a motor (not shown) and generates a vacuum as is well known to those skilled in the art. The vacuum pump 98 is in fluid communication with the cavity 40 of the handheld unit 34. The vacuum pump 98 provides suction in the cavity 40 such that the edge 42 of the housing and/or the seal 46 sealingly engages with the skin when a vacuum is applied.

Preferably, a vacuum manifold 100 is disposed within the cavity 40 to provide an even suction throughout the length of the cavity 40. The vacuum manifold 100 is preferably in fluid communication with the vacuum pump 98 via vacuum tubing and/or a vacuum cylinders (neither numbered) molded into the housing 36. Of course, those skilled in the art realize alternative techniques for providing a vacuum to the cavity 40.

The apparatus 30 also includes a coolant supply 102. The coolant supply 102 is also preferably disposed within the control unit 48. The coolant supply 102 is in fluid communication with the cavity 40 for supplying a coolant directly to the skin. The coolant is preferably not electrically conductive, i.e., a dielectric, such that the coolant will not create electrical arcs between the electrodes 32. The coolant may be deionized water, however other suitable coolants are known to those skilled in the art. A coolant pump (not shown) may be utilized to pump coolant from the coolant supply 102 to the cavity 40. A coolant manifold 104 is preferably disposed within the cavity 40 and in fluid communication with the coolant supply 102 for evenly applying the coolant to the skin.

Preferably, the handheld unit 34 includes a plurality of pushbuttons 105 for controlling operation of the apparatus 30. The pushbuttons 105 are preferably in communication with the controller 52, i.e., the pushbuttons 105 are electrically connected to the controller 52. The pushbuttons 105, working in coordination with the controller 52, allow control over the overall power of the apparatus 30, the application of the vacuum, the application of the coolant, and the energization of the electrodes 32. Of course, those skilled in the art realize other suitable user interfaces for control of the apparatus 30 besides the preferred pushbuttons 105. The pushbuttons 105 may include light emitting diodes (LEDs) (not shown) or other light generating sources to provide feedback to the user as to the status of the overall power, vacuum, coolant, and electrodes 32. The control panel 48 may also include a display 132 for also displaying these statuses, as well as other aspects of the apparatus 30. Furthermore, a speaker (not shown) may be integrated with the handheld device 34 or the control panel 48 to provide audible feedback to apparatus 30 functionality.

As mentioned above, the apparatus 30 may be utilized in skin tightening procedures. To begin the procedure, the handheld unit 34 is positioned such that the opening 44 is disposed over the area of skin to be treated. Accordingly, the edge 42 and/or seal 46 is placed in contact with the skin. The vacuum pump 98 is activated, preferably using the pushbuttons 105. When the vacuum pump 98 is activated, a vacuum suction occurs within the cavity 40. The edge 42 and/or seal 46 thus sealingly engage the skin. When the vacuum is sufficient, the electrode positioning mechanism 74 is pushed inwards toward the cavity 40. The mechanism 74 engages the electrodes 32, moving them from the first position to the second position. The electrodes 32 pierce the skin during this movement. Preferably, the electrodes 32 penetrate the skin to a maximum depth of about 0.8 to 2.3 mm when in the second position. As stated above, it is preferred that only 0.5 mm of each electrode 32 is not coated with the dielectric coating and thus is able to conduct electricity to the skin. For the skin tightening procedure, it is preferred that this exposed portion of the electrodes 32 is disposed in the subcutaneous layer of the skin. The second proximity sensor 96 senses when the mechanism 74 is fully extended, and thus all electrodes 32 are in the second position.

After all of the electrodes 32 are extended, the coolant may then be applied to the skin. Preferably, the controller 52 will activate the coolant pump in sequence when the appropriate pushbutton 105 is pressed. However, the controller 52 preferably prevents coolant application until the mechanism 74 is in the second position and the vacuum is maintained. Alternatively, the controller 52 may automatically apply the coolant once the mechanism 74 reaches the second position without activation of the pushbutton 105.

The coolant disperses from the coolant manifold 104 which is on the opposite side of the cavity 40 from the vacuum manifold 100. Accordingly, the coolant is suctioned across from the coolant manifold 104, across the skin, and into the vacuum manifold 100. Thus, coolant is applied directly and evenly to all portions of the skin within the edges 42. Since the coolant is applied directly to the skin, it is very effective in cooling the outer layer of the skin during the procedure.

The vacuum pump 98 and coolant supply 102 may be interconnected to recover coolant used in the procedure. Alternatively, the coolant used in the procedure may be disposed of to avoid contamination.

Once coolant is circulating, the electric current is then applied to the skin via the electrodes 32. Preferably, activation of the electrodes 32 is via the appropriate pushbutton 105. However, application of the electric current may be automatic after application of the coolant. As stated above, the electric current is supplied as an RF signal. In one technique, the electric current may be activated and maintained for a set length of time. In another technique, the electric current may be deactivated based on a measured resistance of the skin, as is well known to those skilled in the art. The coolant continues to flow while the electric current is activated, to cool the skin while being heated by the electrodes 32.

Once the electric current is deactivated, the coolant may be deactivated as well. Next, the electrodes 32 are preferably retracted to their first position by moving the mechanism 86 from the second position back to the first position. Finally, the vacuum is deactivated and the handheld unit 34 is removed from the patient's skin. Of course, the handheld unit 34 may be repositioned on other areas of the skin to repeat the procedure as necessary.

The apparatus 30 creates mechanical and thermal injuries to the skin. As these injuries heal, the effect is tightening of the skin, which is normally perceived to be the appearance of younger and tighter skin.

In a second embodiment, as shown in FIGS. 12-18, each electrode 32 is part of an individualized capsule 106 preferably having a cylindrical shape. The capsule 106 acts as the electrode carrier. Referring specifically to FIG. 15, each capsule 106 is formed as a unitary part formed of a metal, such as stainless steel. The electrode 32 extends from a disc 108. The disc and portions of the electrode are coated with the dielectric coating to prevent electric current from flowing out of the disc 108 or coated portions of the electrode 32.

As described above, about 0.5 mm of each electrode, at the tip end of the electrode 32, is uncoated. A throat 110 extends from the other side of the disc 108 opposite of the electrode 32 and a shoulder 112 extends from the throat 110. The throat 110 has a diameter that is less than a diameter of the plate 108 and the shoulder 112. The throat 110 and shoulder 112 are not covered with the dielectric coating such that electric current may flow though them. Each capsule 106 defines a slot 114 extending through the shoulder 112 and into the throat 110. The slot 114 allows the capsule 106 to be compressed for removal as described below. The shoulder 112 of each capsule 106 also defines a beveled top edge 116. The beveled top edge 116 of the capsule 106 engages with the angled surface 84 of the electrode positioning mechanism 74.

Referring to FIG. 16, the handheld unit 34 of the second embodiment also includes at least one plate 118 for supporting the capsules 106. The plate 118 is preferably formed of plastic or other non-conductive material. Alternatively, the plate may be formed of a metal and coated to prevent electrical conduction. The plate 118 defines a plurality of holes 120. The diameter of each hole 120 is sized larger than the diameter of the throat 110 of each capsule 106, but smaller than the diameter of the disc 108 and the shoulder 112. Accordingly, the throat 110 of the capsule may slidably engage the plate 118 to move between the first and second positions. Each capsule 106 may be removed from the plate 118 by compressing the capsule 106 as described above.

The plate 118 also defines recesses 122 that encompass a plurality of holes 120, such as a row or column of holes 120. The recesses 122 each accommodate a conductive strip 124, as shown in FIG. 17. Each conductive strip 124 is formed of a conductive material, such as metal, and also defines a plurality of holes 126 that align with the holes 120 of the plate 118. Therefore, each capsule 106 slidably engages both the plate 118 and the conductive strip 124. Accordingly, the capsules 106 and electrodes 32 in each row (or column) are electrically connected together. At least one coil 92 extends from a top of each conductive strip 124. As in the first embodiment, the coil 92 in the second embodiment functions to return the electrodes 32 to the first position after retreat of the electrode positioning mechanism 74. Likewise, the coil 92 serves as the electrical contact between the conductive strip 124 and the wire 51, as shown in FIG. 18.

In a third embodiment, as shown in FIGS. 19-22, the electrodes 32 are supported by and project from a block 128. The block acts as the electrode carrier. The block 128 is formed of a flexible material allowing it to curve and bend, as can be seen in FIG. 19. Preferably, the electrodes 32 are divided into a groups (not numbered) of electrodes 32 that are electrically connected together within the block 128. Each group includes a pin 130 extending out of the block 128 for electrical connection to the power supply. The groups of electrodes 32 may be arranged in rows or columns or other suitable patterns.

The present invention has been described herein in an illustrative manner, and it is to be understood that the terminology which has been used is intended to be in the nature of words of description rather than of limitation. Many modifications and variations of the invention are possible in light of the above teachings. The invention may be practiced otherwise than as specifically described within the scope of the appended claims.

What is claimed is:

1. An electrosurgical apparatus for applying electrical current to skin, said electrosurgical apparatus comprising:

a housing having an edge defining an opening, wherein said edge includes a plurality of edge segments, and wherein said plurality of edge segments are coplanar with one another;

a handle portion connected to said housing, wherein said handle portion defines a channel;

a plurality of electrodes for conveying the electrical current to the skin, wherein each of said plurality of electrodes is movable between a first position and a second position, and wherein said plurality of electrodes are configured to penetrate the skin in said second position;

an electrode positioning mechanism comprising a slidable body including a proximal end and a distal end, wherein said distal end of said slidable body includes a sliding surface configured to slide against each of said plurality of electrodes in order to move each of said of plurality of electrodes from said first position to said second position and back to said first position as said proximal end of said slidable body slides within and physically contacts at least one surface of said channel.

2. The electrosurgical apparatus as set forth in claim 1 wherein each of said plurality of electrodes are generally perpendicular with said edge when said plurality of electrodes are in said second position.

3. The electrosurgical apparatus as set forth in claim 1 further comprising at least one electrode carrier wherein said at least one electrode carrier supports at least one of said plurality of electrodes.

4. The electrosurgical apparatus as set forth in claim 3 wherein said sliding surface is capable of engaging said at least one electrode carrier as said slidable body slides along said channel in a first direction to move at least one of said plurality of electrodes between said first position and said second position, wherein said plurality of electrodes move between said first position and said second position in a second direction, with said first direction being substantially perpendicular to said second direction.

5. The electrosurgical apparatus as set forth in claim 4, wherein when the at least one electrode carrier moves in an opposite direction, the electrodes move toward said first position.

6. The electrosurgical apparatus as set forth in claim 1 wherein said plurality of electrodes are configured to penetrate the skin to a maximum depth of from 0.8 to 2.3 mm in said second position.

7. The electrosurgical apparatus as set forth in claim 6 wherein said plurality of electrodes are configured to extend into a subcutaneous layer of the skin in said second position.

8. The electrosurgical apparatus as set forth in claim 1 wherein said electrode positioning mechanism operatively slides against at least two of said plurality of electrodes simultaneously such that said at least two of said plurality of electrodes move between said first position and said second position in unison.

9. The electrosurgical apparatus as set forth in claim 1 wherein said sliding surface comprises an angled surface.

10. The electrosurgical apparatus as set forth in claim 1 wherein said slidable body comprises a flexible material.

11. The electrosurgical apparatus as set forth in claim 1 wherein said slidable body comprises an engagement tab, wherein said engagement tab is capable of mechanically engaging said handle portion.

12. An electrosurgical apparatus for applying electrical current to skin, said electrosurgical apparatus comprising:

a housing having an edge defining an opening, wherein said edge includes a plurality of edge segments, and wherein said plurality of edge segments are coplanar with one another;

a handle portion connected to said housing, wherein said handle portion defines a channel;

a plurality of electrodes for conveying the electrical current to the skin, wherein each of said plurality of electrodes is movable between a first position and a second position, and wherein said plurality of electrodes are configured to penetrate the skin in said second position; and an electrode positioning mechanism comprising a slidable body including a proximal end and a distal end, wherein said distal end of said slidable body includes a sliding surface configured to slide against each of said plurality of electrodes in order to move each of said of plurality of electrodes between said first position and said second position as said proximal end of said slidable body slides within and physically contacts at least one surface of said channel;

wherein each of said plurality of electrodes is at least partially coated with a dielectric coating such that an uncoated portion of each of said plurality of electrodes is capable of providing the electric current primarily to a subcutaneous layer of the skin.

13. An electrosurgical apparatus for applying electrical current to skin, said electrosurgical apparatus comprising:

a housing defining a cavity;

said housing having an edge defining an opening to said cavity;

a handle portion connected to said housing, wherein said handle portion defines a channel;

a plurality of electrodes supported by said housing for conveying the electrical current to the skin, wherein each of said plurality of electrodes is movable between a first position in which each of said plurality of electrodes is completely contained within said cavity and a second position in which each of said plurality of electrodes extends through said opening, wherein said plurality of electrodes are configured to penetrate the skin in said second position;

an electrode positioning mechanism comprising a slidable body including a proximal end and a distal end, and wherein said distal end of said slidable body includes a surface configured to engage and disengage each of said plurality of electrodes with movement of the slidable body in order to move each of said plurality of electrodes separately and individually from said first position to said second position and back to said first position as said proximal end of said slidable body slides within and physically contacts at least one surface of said channel; and a vacuum pump in fluid communication with said cavity such that said housing is configured to sealingly engage with the skin when a vacuum is applied.

14. The electrosurgical apparatus as set forth in claim 13 further comprising a vacuum manifold disposed within said cavity and in fluid communication with said vacuum pump for providing suction in said cavity.

15. An electrosurgical apparatus for applying electrical current to skin, said electrosurgical apparatus comprising:

a housing defining a cavity;

said housing having an edge defining an opening to said cavity;

a handle portion connected to said housing, wherein said handle portion defines a channel:

a plurality of electrodes supported by said housing for conveying the electrical current to the skin, wherein each of said plurality of electrodes is movable between a first position in which each of said plurality of electrodes is completely contained within said cavity and a second position in which each of said plurality of electrodes extends through said opening, wherein said plurality of electrodes are configured to penetrate the skin in said second position;

an electrode positioning mechanism comprising a slidable body including a proximal end and a distal end, and wherein said distal end of said slidable body includes a surface configured to engage and disengage each of said plurality of electrodes with movement of the slidable body in order to move each of said plurality of electrodes separately and individually between said first position and said second position as said proximal end of said slidable body slides within and physically contacts at least one surface of said channel;

a vacuum pump in fluid communication with said cavity such that said housing is configured to sealingly engage with the skin when a vacuum is applied; and a coolant manifold in fluid communication with said cavity for supplying a coolant temporarily to the skin and removing said coolant.

16. The electrosurgical apparatus as set forth in claim 15 further comprising the coolant manifold disposed within said cavity and in fluid communication with said coolant supply for applying the coolant to the skin and removing said coolant from the skin.

17. An electrosurgical apparatus for applying electrical current to skin, said electrosurgical apparatus comprising:
a housing defining a cavity;
said housing having an edge defining an opening to said cavity;
a handle portion connected to said housing, wherein said handle portion defines a channel:
a plurality of electrodes supported by said housing for conveying the electrical current to the skin, wherein each of said plurality of electrodes is movable between a first position in which each of said plurality of electrodes is completely contained within said cavity and a second position in which each of said plurality of electrodes extends through said opening, wherein said plurality of electrodes are configured to penetrate the skin in said second position;
an electrode positioning mechanism comprising a slidable body including a proximal end and a distal end, and wherein said distal end of said slidable body includes a surface configured to engage and disengage each of said plurality of electrodes with movement of the slidable body in order to move each of said plurality of electrodes separately and individually between said first position and said second position as said proximal end of said slidable body slides within and physically contacts at least one surface of said channel; and
a vacuum pump in fluid communication with said cavity such that said housing is configured to sealingly engage at an edge with the skin when a vacuum is applied, wherein said edge includes a seal formed of an elastomeric material.

18. The electrosurgical apparatus as set forth in claim 17 wherein said seal is disposed along a periphery of the housing.

19. An electrosurgical apparatus for applying electrical current to skin, said electrosurgical apparatus comprising:
a housing defining a cavity;
said housing having an edge defining an opening to said cavity;
a handle portion connected to said housing, wherein said handle portion defines a channel;
a plurality of electrodes supported by said housing for conveying the electrical current to the skin, wherein each of said plurality of electrodes is movable between a first position and a second position, and wherein said plurality of electrodes are configured to penetrate the skin in said second position;
an electrode positioning mechanism comprising a slidable body including a proximal end and a distal end, wherein said distal end of said slidable body includes a slidable surface configured to contact each of said plurality of electrodes in order to move each of said plurality of electrodes between said first position and said second position and back to the first position as said proximal end of said slidable body slides within and physically contact at least one surface of said channel to engage and disengage each of said plurality of electrodes; and
a coolant in fluid communication with said cavity such that the coolant is directly applied temporarily to the skin and at least substantially removed from the skin during operation of said electrosurgical apparatus.

20. The electrosurgical apparatus as set forth in claim 19 wherein said plurality of electrodes are configured to penetrate the skin to a maximum depth of from 0.8 to 2.3 mm in the second position.

21. The electrosurgical apparatus as set forth in claim 20 wherein said plurality of electrodes are configured to extend into a subcutaneous layer of the skin in said second position.

22. The electrosurgical apparatus as set forth in claim 19 wherein said edge includes a seal formed of an elastomeric material and said seal is disposed along a periphery of the housing.

23. An electrosurgical apparatus for applying electrical current to skin, said electrosurgical apparatus comprising:
a housing defining a cavity;
said housing having an edge defining an opening to said cavity;
a handle portion connected to said housing, wherein said handle portion defines a channel:
a plurality of electrodes supported by said housing for conveying the electrical current to the skin, wherein each of said plurality of electrodes is movable between a first position and a second position, and wherein said plurality of electrodes are configured to penetrate the skin in said second position;
an electrode positioning mechanism comprising a slidable body including a proximal end and a distal end, wherein said distal end of said slidable body includes a slidable surface configured to contact each of said plurality of electrodes in order to move each of said plurality of electrodes between said first position and said second position and back to the first position as said proximal end of said slidable body slides within and physically contacts at least one surface of said channel to engage and disengage each of said plurality of electrodes; and
a coolant supply in fluid communication with said cavity such that a coolant is directly applied temporarily to the skin;
wherein each of said plurality of electrodes is at least partially coated with a dielectric coating such that an uncoated portion of each of said plurality of electrodes is capable of providing the electric current primarily to the subcutaneous layer.

24. An electrosurgical apparatus for applying electrical current to skin, said electrosurgical apparatus comprising:
a housing having an edge defining an opening, wherein said edge includes a plurality of edge segments, and wherein said plurality of edge segments are coplanar with one another:
a handle portion connected to said housing, wherein said handle portion defines a channel;
plurality of electrodes for conveying the electrical current to the skin, wherein each of said plurality of electrodes is movable between a first position and a second position, and wherein said plurality of electrodes are configured to penetrate the skin in said second position;
an electrode positioning mechanism comprising a slidable body including a proximal end and a distal end, wherein said distal end of said slidable body includes a sliding surface configured to slide against each of said plurality of electrodes in order to move each of said of plurality of electrodes between said first position and said second position as said proximal end of said slidable body slides within and physically contacts at least one surface of said channel;
wherein said edge includes a seal formed of an elastomeric material and said seal is disposed along a periphery of said housing.

25. A method of applying electrical current to skin, said method comprising:
providing an electrosurgical apparatus comprising: a housing having an edge defining an opening, wherein said edge includes a plurality of edge segments, and wherein said plurality of edge segments are coplanar with one another; a handle portion connected to said housing, wherein said handle portion defines a channel; a plurality of electrodes for conveying the electrical current to the skin, wherein each of said plurality of electrodes is movable between a first position and a second position, and wherein said plurality of electrodes are configured to penetrate the skin in said second position; an electrode positioning mechanism comprising a slidable body including a proximal end and a distal end, wherein said distal end of said slidable body includes a sliding surface configured to slide against each of said plurality of electrodes in order to move each of said of plurality of electrodes from said first position to said second position and back to said first position as said proximal end of said slidable body slides within and physically contacts at least one surface of said channel;
sliding the proximal end of the slidable body within the channel such that the proximal end of the slidable body physically contacts the at least one surface of the channel and that the second sliding surface of the slidable body engages at least one of the plurality of electrodes to move the at least one of the plurality of electrodes between the first position and the second position;
penetrating the skin with the plurality of electrodes without extending through a dermis layer; and
delivering electrical current to the skin with the plurality of electrodes.

* * * * *